United States Patent [19]

Elsayed et al.

[11] Patent Number: 6,045,501

[45] Date of Patent: Apr. 4, 2000

[54] METHODS FOR DELIVERING A DRUG TO A PATIENT WHILE PREVENTING THE EXPOSURE OF A FOETUS OR OTHER CONTRAINDICATED INDIVIDUAL TO THE DRUG

[75] Inventors: Marc Elsayed, Bridgewater; Bruce Williams, Flemington, both of N.J.

[73] Assignee: Celgene Corporation, Warren, N.J.

[21] Appl. No.: 09/143,569

[22] Filed: Aug. 28, 1998

[51] Int. Cl.⁷ .................................................. A61N 5/00
[52] U.S. Cl. ........................ 600/300; 600/304; 600/551
[58] Field of Search .................................... 434/262, 272, 434/273; 600/300–301, 304, 313, 338, 376, 511, 551; 128/920–925, 897–898

[56] References Cited

U.S. PATENT DOCUMENTS 5,299,121  3/1994  Brill et al. .............................. 600/301
5,594,637  1/1997  Eisenberg et al. ...................... 600/300
5,619,991  4/1997  Sloane .................................... 600/300
5,660,176  8/1997  Iliff ......................................... 600/300

*Primary Examiner*—Cary O'Connor
*Assistant Examiner*—Michael Astarino
*Attorney, Agent, or Firm*—Woodcock Washburn Kurtz Mackiewicz & Norris LLP

[57] ABSTRACT

Novel methods for delivering a drug to a patient while preventing the exposure of a foetus or other contraindicated individual to the drug. Embodiments are provided in which the involved prescribers, pharmacies and patients are registered in one or more computer databases. Embodiments are also provided in which registered patients receive counseling information concerning the risks attendant to foetal exposure to the drug. Male patients and female patients who are not pregnant may, in certain circumstances, receive the drug.

10 Claims, No Drawings

METHODS FOR DELIVERING A DRUG TO A PATIENT WHILE PREVENTING THE EXPOSURE OF A FOETUS OR OTHER CONTRAINDICATED INDIVIDUAL TO THE DRUG

FIELD OF THE INVENTION

The present invention relates to novel methods for delivering a drug to a patient. More particularly, the present invention relates to novel methods for delivering a teratogenic or other potentially hazardous drug to a patient while preventing the exposure of a person, such as a foetus, to the drug when such exposure is contraindicated. The novel methods permit the distribution to patients of drugs, particularly teratogenic drugs, in ways wherein such distribution can or must be carefully monitored and controlled.

BACKGROUND OF THE INVENTION

Thalidomide is a drug which was first synthesized in Germany in 1957. Beginning in 1958, it was marketed in many countries for use as a sedative, although it was never approved for use in the United States. After reports of serious birth defects, thalidomide was withdrawn from all markets by 1962. However, during the years it was used, it was found to be effective in treating erythema nodosum leprosum (ENL), a condition of leprosy, and the U.S. Food and Drug Administration (FDA) has made the drug available for this specific use via a program of the Public Health Service. More recently, investigators have found that thalidomide may be effective in treating AIDS wasting and aphthous ulcers occurring in AIDS patients. In addition, treatments for other diseases, such as a number of serious diseases including cancers, inflammatory bowel diseases, Behcet's Disease, rheumatoid arthritis, and macular degeneration, are also believed to be possible. The FDA has recently approved an application by Celgene Corporation, which is the assignee of the present patent application, to market thalidomide for the treatment of ENL. The medical community anticipates that thalidomide will be used for treatment of additional conditions and diseases, including those set forth above. However, due to the severe teratogenic risk of thalidomide, methods are needed to control the distribution of this drug so as to preclude administration to foetuses. Methods for distribution of other potentially hazardous drugs are also needed to guard against improper provision to persons for whom such drug is contraindicated.

Previous methods for controlling the distribution of drugs have been developed in connection with Accutane (isotretinoin). Accutane, which is a known teratogen, is a uniquely effective drug for the treatment of severe, recalcitrant, nodular acne. A pregnancy prevention program was developed, and the Slone Epidemiology Unit of Boston University designed and implemented a survey to evaluate these efforts. The survey identified relatively low rates of pregnancy during Accutane treatment, which suggests that such a program can be effective. With more than about 325,000 women enrolled to date in the Accutane survey, it is also clear that such a large-scale study can be conducted. However, enrollment in the Accutane survey is voluntary. Accordingly, assessing the representativeness of the women who have been enrolled in the survey has been problematic, and it has been difficult to determine whether the survey results can be generalized to all female Accutane users.

Thus, improved methods are needed which are more representative of all users of a particular drug, such as thalidomide, who obtain the involved drug through lawful distribution channels. Also, because drug sharing may frequently occur, such as among AIDS patients, which may result in placing a fetus at risk, a program is needed which can be used to educate men and women about the risk of teratogenic drugs, such as thalidomide. The present invention is directed to these, as well as other important ends.

SUMMARY OF THE INVENTION

The present invention is directed to methods for the delivery of potentially hazardous drugs, such as teratogenic drugs, to patients. In one embodiment of the invention, there are provided methods for delivering a teratogenic drug to patients in need of the drug while avoiding the delivery of said drug to a foetus comprising:

a. registering in a computer readable storage medium prescribers who are qualified to prescribe said drug;

b. registering in said medium pharmacies to fill prescriptions for said drug;

c. registering said patients in said medium, including information concerning the ability of female patients to become pregnant and, optionally, the ability of male patients to impregnate females;

d. retrieving from said medium information identifying a subpopulation of said female patients who are capable of becoming pregnant and, optionally, male patients who are capable of impregnating females;

e. providing to the subpopulation, counseling information concerning the risks attendant to fetal exposure to said drug;

f. determining whether patients comprising said subpopulation are pregnant; and g. in response to a determination of non-pregnancy for said patients, authorizing said registered pharmacies to fill prescriptions from said registered prescribers for said non-pregnant registered patients.

Another embodiment of the invention relates to methods for delivering a potentially hazardous drug to patients in need of the drug while avoiding the delivery of said drug to persons for whom said drug is contraindicated comprising:

a. registering in a computer readable storage medium prescribers who are qualified to prescribe said drug;

b. registering in said medium pharmacies to fill prescriptions for said drug;

c. registering said patients in said medium, including information concerning the likelihood of said patients having a condition which contraindicates exposure to the drug;

d. retrieving from said medium information identifying a subpopulation of said patients who have a condition which contraindicates exposure to the drug;

e. providing to the subpopulation, counseling information concerning the risks attendant to exposure to said drug;

f. determining whether patients comprising said subpopulation have said condition; and g. in response to a determination that said patients do not have said condition, authorizing said registered pharmacies to fill prescriptions from said registered presicrbers for said registered patients for whom said drug is not contraindicated.

The methods described herein provide advantageous and effective means for monitoring, controlling and authorizing the distribution of drugs to patients, particularly teratogenic drugs. The methods of the present invention include a variety of checks and controls which serve to limit unauthorized and possibly inappropriate distribution of the drug. In the case of teratogenic drugs, the checks and balances may be particularly advantageous for preventing distribution of the drug to patients whose use of the drug may pose an unacceptable risk of foetal exposure. Accordingly, the present methods may be advantageously used to avoid exposure of foetuses to teratogenic drugs, thereby avoiding the terrible birth defects which may result from such exposure.

The invention is not limited to the distribution of teratogenic drugs; other potentially hazardous drugs may also be distributed in accordance with embodiments of this invention and such drugs may be distributed in such a fashion that persons for whom such drugs are contraindicated will not receive them. These and other aspects of the invention will become more apparent from the present description and claims.

DETAILED DESCRIPTION OF PREFERRED EMBODIMENTS

The present invention is directed generally to methods for the delivery of drugs, especially teratogenic drugs, to patients. The term "drug," as used herein, refers to any substance which is intended for use in the diagnosis, cure, mitigation, treatment or prevention of disease, or to affect the structure or function of the body. Generally speaking, the methods of the present invention may be desirably and advantageously used to educate and reinforce the actions and behaviors of patients who are taking the drug, as well as prescribers who prescribe the drug and pharmacies which dispense the drug. As used herein, the term "prescriber" refers to any individual who are capable of prescribing drugs, including, for example medical doctors. Such education and reinforcement of actions and behavior are often necessary to ensure proper prescribing and dispensing of the drug, as well as patient compliance with taking the drug. A wide variety of educational materials may be employed to ensure proper prescribing, dispensing and patient compliance according to the methods described herein, including, for example, a variety of literature and other materials, such as, for example, product information, educational brochures, continuing education monographs, videotapes and the like which may describe the risks and benefits associated with taking the particular drug.

The methods described herein may be advantageously employed for the delivery of a drug to a patient for whom the drug is contraindicated. As used herein, the term "contraindicated" refers to any condition in a patient which renders a particular line of treatment, including the administration of one or more drugs, undesirable or improper. Thus, contraindicated drugs include, for example, teratogenic drugs whose administration, for example, to pregnant patients is importantly avoided due to the risks to the foetus. The methods of the present invention are especially advantageously employed for the delivery to a patient of a teratogenic drug. The delivery of a teratogenic drug to a patient may be advantageously achieved with the present methods while substantially (including completely) avoiding the delivery of the drug to a foetus (i.e., fetus). The term "substantially," as used in reference to avoiding the delivery of a teratogenic drug to a foetus, generally means that there is an avoidance rate of delivering the drug to a foetus of greater than about 50%. Preferably, the avoidance rate is greater than about 55%, with an avoidance rate of greater than about 60% being more preferred. Even more preferably, the avoidance rate is greater than about 65%, with an avoidance rate of greater than about 70% being still more preferred. Yet more preferably, the avoidance rate is greater than about 75%, with an avoidance rate of greater than about 80% being still more preferred. In even more preferred embodiments, the avoidance rate is greater than about 85%, with an avoidance rate of greater than about 90% being yet more preferred. Still more preferably, the avoidance rate is greater than about 95%. In particularly preferred embodiments, a teratogenic drug may be delivered to patients with substantially no delivery to foetuses (i.e., nearly 100% avoidance rate).

The drug delivery methods of the present invention preferably involve, inter alia, registering in a computer readable storage medium prescribers who are qualified to prescribe the involved drug including, for example, teratogenic drugs. Once registered in the computer readable storage medium, the prescriber may be eligible to prescribe the drug to patients in need of the drug. Generally speaking, in order to become registered in the computer readable storage medium, the prescriber may be required to comply with various aspects of the methods described herein including, for example, providing patient education and counseling, and the like, as described in detail below. The registration of the prescriber in the computer readable storage medium may be achieved by providing the prescriber, for example, by mail, facsimile transmission, or on-line transmission, with a registration card or form, preferably together with appropriate educational materials concerning, for example, the particular drug for which the prescriber is being registered to prescribe, as well as suitable methods for delivering the drug to the patient, including the drug delivery methods described herein. The prescriber will preferably complete the registration card or form by providing information requested therein, and the registration card or form will preferably be returned to the manufacturer or distributor of the drug, or other authorized recipient of the registration materials, for example, by mail, facsimile transmission or on-line transmission. Information which may be requested of the prescriber in the registration card or form may include, for example, the prescriber's name, address, and affiliation, if any, with one or more health care institutions. The prescriber's information in the registration card or form is then entered into the computer readable storage medium. It is contemplated that the registration of the prescriber into the computer readable storage medium may also be achieved, for example, by telephone. Suitable computer readable storage media which may be employed for registration of the prescribers (as well as the pharmacies and patients, as discussed below) will be apparent to one of ordinary skill in the art, once armed with the teachings of the present application.

In accordance with the methods described herein, pharmacies which may fill prescriptions for the particular drug being prescribed including, for example, teratogenic drugs, are also preferably registered in a computer readable storage medium. The computer readable storage medium in which the pharmacies are registered may be the same as, or different from the computer readable storage medium in which the prescribers are registered. Once registered in the computer readable storage medium, the pharmacies may be eligible to dispense the involved drug to patients who are in need of the drug. Generally speaking, in order to become registered in the computer readable storage medium, the pharmacy may be required to comply with various aspects of the methods described herein including, for example, registering the patient (preferably also in a computer readable storage medium), as well as other aspects of the present methods, as described in detail below. As with the registration of the prescriber in the computer readable storage medium, the registration of the pharmacy may be achieved by providing the pharmacy, for example, by mail, facsimile transmission, or on-line transmission, with a registration card or form, preferably together with appropriate educational materials concerning, for example, the particular drug for which the pharmacy is being registered to dispense, as well as suitable methods for delivering the drug to the patient, including the drug delivery methods described herein. The pharmacy may then have the registration card or form completed by providing the information requested therein, which thereafter may be returned to the manufacturer or distributor of the drug, or other authorized recipient of the registration card or form, for example, by mail, facsimile transmission or on-line transmission. Information which may be requested of the pharmacy in the registration card or form may include, for example, the pharmacy's name, address, and affiliation, if any, with any health care institution such as, for example, hospital, health care organization, and the like. The pharmacy's information in the registration card or form is then preferably entered into the computer readable storage medium. It is contemplated that the registration of the pharmacy into the computer readable storage medium may also be achieved, for example, by telephone.

As noted above, the drug delivery methods described herein also preferably involve the registration of the patient in a computer readable storage medium. As discussed below, the registration of the patient is preferably carried out by the registered pharmacy at the time of the patient's initial visit to the pharmacy. The computer readable storage medium in which the patients are registered may be the same as, or different from the computer readable storage medium in which the prescriber and/or pharmacy is registered. Once registered in the computer readable storage medium, the patient in need of a particular drug including, for example, a particular teratogenic drug, may be eligible to receive the drug. Generally speaking, in order to become registered in the computer readable storage medium, the patient may be required to comply with various aspects of the methods described herein. In preferred form, the pharmacy will typically have a registration form filled out for the patient, which includes information on the patient, such as the patient's name, mailing address, date of birth, and the like. Information on the prescribing prescriber and dispensing pharmacy, such as the information described above for the registration thereof, may also be desirably entered on the patient registration form. The completed form may then be forwarded to the manufacturer or distributor of the drug, or other authorized recipient of the registration form, for example, by mail, facsimile transmission or on-line transmission. It is contemplated that the registration of the patient into the computer readable storage medium may also be achieved, for example, by telephone.

In accordance with the methods of the present invention, the delivery of the drug to the patient may involve the following steps. As a prelude to prescribing and dispensing the drug to the patient, the prescriber and the pharmacy are registered in one or more appropriate computer readable storage media, as described above. If the prescriber is not registered in the computer readable storage medium, the prescriber will be ineligible to prescribe the drug. Similarly, if the pharmacy is not registered in the computer readable storage medium, the pharmacy will be ineligible to dispense the drug.

In the course of an examination of a patient, including patients suffering from one or more diseases and/or disorders such as, for example, erythema nodosum leprosum (ENL), the prescriber may determine that the patient's condition would be improved by the administration of a drug such as, for example, a teratogenic drug, including thalidomide. Prior to prescribing the drug, the prescriber preferably counsels the patient, for example, on the various risks and benefits associated with the drug. For example, the prescriber preferably discusses the benefits associated with taking the drug, while also advising the patient on the various side effects associated therewith. Thus, a patient who may acquire or impart a condition or disease for which the drug is contraindicated is preferably counseled by the prescriber on the dangers associated therewith. For example, in the case of teratogenic drugs, the prescriber preferably counsels the patient on the dangers of exposing a foetus to the teratogenic drug. Such counsel may be provided verbally, as well as in written form. In preferred embodiments, the prescriber provides the patient with literature materials on the drug for which a prescription is contemplated, such as product information, educational brochures, patient instruction videos, and the like. Thus, in the case of methods involving teratogenic drugs, the prescriber preferably provides patients with literature information, for example, in the form of the aforesaid product information, educational brochures, patient instruction videos, and the like, warning the patient of the effects of the drug on foetuses.

With particular reference to counseling provided in connection with teratogenic drugs, the prescriber preferably counsels female patients that such drugs must never be used by pregnant women. If the patient is a female of childbearing potential (i.e., a woman who is capable of becoming pregnant), the prescriber preferably counsels the patient that even a single dosage of certain teratogenic drugs, such as thalidomide, may cause birth defects. Accordingly, the patient is preferably counseled to avoid sexual intercourse entirely, or if sexually active, to use appropriate forms of contraception or birth control. For both male and female patients, the prescriber preferably provides counsel on the importance of using at least two forms of effective birth control methods, with one form preferably being a highly effective hormonal method, and the other from preferably being an effective barrier method. The patients are preferably counseled to use the birth control methods for a period of time prior to and during treatment with the teratogenic drug, as well as for a period of time after treatment with the drug has been terminated. In preferred embodiments, the patient is counseled to use at least two forms of birth control for at least about 4 weeks prior to initiation of treatment, during treatment, and for at least about 4 weeks after treatment has been terminated. It may be desirable for the prescriber to personally provide female patients who are capable of becoming pregnant with a contraceptive device or formulation.

Male patients who are being prescribed a teratogenic drug are preferably counseled to use condoms every time they engage in sexual relations, since many teratogenic drugs may be found in semen. Male patients are also preferably counseled to contact their prescriber if they have sexual intercourse without a condom, and/or if it is believed that they may have caused a pregnancy. As with female patients, it may be desirable for the prescriber to provide male patients who are capable of impregnating female patients with a contraceptive device or formulation. Other advice relative to birth control that the prescriber may provide to the patient would be apparent to one skilled in the art, once armed with the teachings of the present application. If the prescriber who is prescribing the teratogenic drug is unaware of certain aspects of the available forms of birth control and the advantages and disadvantages associated therewith, the patient should be referred to a prescriber who is knowledgeable on such matters, prior to be being prescribed the involved drug. Generally speaking, as discussed below, counseling on teratogenecity, birth control, and the like is preferably given only to female patients who are capable of becoming pregnant, or to male patients who are capable of impregnating female patients. In this manner, unnecessary counseling, for example, to women who are no longer of child-bearing age or men who are incapable of impregnating women, may be avoided.

With further reference to methods involving teratogenic drugs, it is also preferred that the prescriber advise the patient to not share the drug with anyone else, and particularly that the drug should be kept out of the reach of children as well as women of child-bearing potential. In the case of female patients, particularly female patients of child-bearing potential, the prescriber should give the patient a pregnancy test, preferably a serum pregnancy test, prior to and during treatment with the teratogenic drug. To begin receiving the teratogenic drug and to continue taking the drug, female patients of child-bearing potential should continue to have negative pregnancy tests. The patient is also preferably counseled by the prescriber to discard or return to the prescriber, pharmacy, manufacturer or distributor any unused portion of the prescribed drug.

As would be apparent to one of ordinary skill in the art, once armed with the teachings of the present application, one or more aspects of the counseling described above may be applicable, in certain circumstances, for drugs other than teratogenic drugs.

In addition to receiving counseling on the drug being prescribed, including counseling, for example, on birth control, and prior to receiving a prescription for the drug, the methods of the present invention preferably involve requiring the patient to fill out an informed consent form which is signed by the prescriber, as well as the patient. The prescriber should retain a copy of the informed consent form for his/her records. By filling out and signing an informed consent form, the patient acknowledges that he/she understands the risks associated with taking the drug. In the informed consent form, the patient preferably agrees to behave in a manner which is consistent with the prescriber's counsel. For example, in cases involving, for example, teratogenic drugs, the patient may agree to use at least one form of birth control, with female patients agreeing to use at least two forms of birth control. In preferred embodiments involving teratogenic drugs, female patients preferably agree also to undergo pregnancy testing, preferably serum pregnancy testing, before, during and after treatment with the teratogenic drug. Female patients preferably will also acknowledge that, at the time they are being prescribed the drug, especially teratogenic drugs, they are not pregnant, they will immediately stop taking the drug if they become pregnant, and they will not try to become pregnant for at least 4 weeks after treatment with the drug is terminated. Female patients, especially female patients for whom a teratogenic drug will be administered, preferably further agree to contact their prescriber if they wish to change one or more of the birth control methods being used and to have an additional pregnancy test if a menstrual period is missed. Female patients, especially female patients to be treated with teratogenic drugs, will preferably agree also to not breastfeed while being treated with the drug.

Male patients who are being prescribed the drugs according to the methods described herein, especially teratogenic drugs, will preferably agree to avoid having unprotected sexual relations with a woman, particularly a woman of child-bearing potential during treatment with the drug. In doing so, male patients will preferably further agree to use a condom during sexual relations with a woman, with latex condoms being preferred. Both male and female patients will also preferably agree to not share the drug with anyone, and to acknowledge that they cannot donate blood while taking the drug, with male patients agreeing also to not donate sperm while taking the drug. In addition, the patients will preferably agree to take part in a confidential patient survey, for example, before, during and after treatment with the drug. The patient survey provides information, for example, to the prescriber, manufacturer and/or distributor of the drug, as well as any group or body which may be established to generally provide oversight on the distribution of the drug, on information regarding the general lifestyle of the patient, including detailed information on the patient's sexual behavior. In this manner, the survey may assist in identifying patients who engage in risky behavior, as well as patients who are non-compliant with the methods described herein. Such risky behavor and/or non-compliance may lead to a suspension or intervention of the patient's treatment with the drug, with re-education being provided to the patient.

The information obtained from the survey is preferably also entered into the computer readable storage medium. Once entered into the computer readable storage medium, the prescriber, manufacturer and/or distributor of the drug may be able to glean therefrom information regarding the level of risk associated with the administration of the involved drug to the various patients. Accordingly, it may be possible to identify, from among the entire population of registered patients, one or more subpopulations of patients for which the involved drug may be more likely to be contraindicated. For example, it may be possible to identify a subpopulation of female patients who are capable of becoming pregnant and/or a subpopulation of male patients who are capable of impregnating female patients. Preferably, the counseling information discussed above relating to exposure of a foetus to a teratogenic drug may then be addressed primarily to this subpopulation of patients.

If the risk is considered to be acceptable, the patient may continue to receive the drug, using the methods described herein. If the risk is considered to be unacceptable, additional counseling may be provided to the patient or, if necessary, treatment of the patient with the involved drug may be terminated, with alternate treatment modalities being provided. In preferred embodiments, female patients will agree to complete a patient survey at least once every month, with male patients agreeing to complete a patient survey at least once every three months.

After the patient has received counseling as described above, and has also filled out and signed an informed consent form, and it is determined that the drug which is to be prescribed is not contraindicated for the patient (such as, for example, a negative pregnancy test in the case of female patients for whom a prescription is desired for a teratogenic drug), the prescriber may prescribe the drug to the patient. In preferred embodiments of the present invention, the amount of the drug which is prescribed to the patient is for a limited amount, preferably no more than about 28 days. Refills for the drug will not be permitted without a renewal prescription from the prescriber, as discussed in detail below. In order to have the prescription filled, the patient preferably presents the prescription and the informed consent form to a pharmacy which has been registered, as discussed above. It is contemplated that the patient may bring the prescription to an unregistered pharmacy. If so, the pharmacy may take steps to become registered, for example, by immediately contacting the manufacturer of the drug. Once registration of the pharmacy is completed, the distribution procedure described herein may resume, per the discussion hereinafter. Of course, this may introduce a delay into the prescription process, and the patient may desire to take the prescription for the drug to an alternate, registered pharmacy. If the patient does not present a completed informed consent form to the pharmacy, the prescription may not be filled. In this case, the pharmacy may contact the prescribing prescriber to have an informed consent form filled out for the patient.

Prior to filling out the prescription and dispensing the drug, the registered pharmacy preferably has a patient registration form filled out for the patient, and the patient is registered in an appropriate computer readable storage medium. The pharmacy may then dispense the drug to the patient. A copy of the patient's informed consent form should be kept for the pharmacy's records. The drug is preferably supplied to the pharmacy (as well as the patient) in packaging, such as individual blister packs, which includes warnings regarding the risks associated with the drug, as well as the importance of various aspects of the present methods such as, for example, pregnancy testing and the use of contraception (in the case of teratogenic drugs), and the dangers associated with sharing the drug with others, among other aspects.

As noted above, the drug is preferably prescribed and dispensed to the patient in a limited amount, with a prescription amount of no more than about 28 days being preferred, and preferably with no refills being permitted. Thus, for the patient to obtain an additional prescription, it is generally necessary for the patient to have a follow-up visit with the prescriber. Such a follow-up visit preferably takes place at least each time the patient requires a renewal of the prescription, and possibly more often if the patient requires, for example, additional counseling. At the follow-up visit, the patient will preferably receive additional counseling regarding the risks and benefits associated with taking the drug, as well as further counseling on birth control (if applicable). The patient will also preferably complete an additional patient survey to provide current information regarding their lifestyle, including their sexual behavior and, if female of childbearing potential, be administered a new pregnancy test. After receiving the counseling and completing the patient survey, and if the pregnancy tests for female patients are negative, the prescriber may fill out a new prescription for the drug. As with the original prescription, the renewal prescription is preferably for a limited period of time, with no more than about 28 days being more preferred.

In preferred embodiments, the prescriber will also receive reminders, for example, via mail, facsimile, or on-line transmission, from the manufacturer, distributor or other group or body providing oversight on drug distribution, that the prescriber has prescribed a hazardous drug to patients which may be contraindicated, and that the involved patients may require additional counseling and pregnancy testing. Such reminders may preferably be delivered to the prescriber, for example, from about 14 to about 21 days after the previous prescription was filled.

As with the original prescription from the prescriber, the patient should present all renewal prescriptions to a registered pharmacy. Prior to filling out the prescription and dispensing the drug, the pharmacy preferably confirms, for example, via a standard on-line transmission or via telephone, that the patient has been registered and is eligible to receive the drug. When patient eligibility has been confirmed, the pharmacy may dispense the drug to the patient. If the patient is ineligible, the pharmacy generally may not dispense the drug to the patient. The pharmacy may then contact, for example, the prescribing prescriber or the manufacturer of the drug to initiate patient registration. In preferred form, the pharmacy will be precluded from dispensing the drug if the patient has more than about 7 days of drug supply from the previous prescription, and/or if the new prescription was written more than about 7 days before the date the patient visits the pharmacy to have it filled.

The registration into one or more computer readable storage media of the prescriber, pharmacy and patient, according to the methods described herein, provide a means to monitor and authorize distribution of contraindicated drugs, including teratogenic drugs. Thus, the computer readable storage media may serve to deny access, dispension or prescriptions of contraindicated drugs, including teratogenic drugs, to patients, pharmacies or prescribers who fail to abide by the methods of the present invention. As noted above, prescribers who are not registered in a computer readable storage medium generally may not prescribe the drug, and pharmacies who are not registered generally may not dispense the drug. Similarly, the drugs generally may not be prescribed and/or dispensed to patients who are not registered in a computer readable storage medium. In addition, patients are also generally required to present an informed consent form to the pharmacy. Unless such a form is presented to the pharmacy, the patient generally may not receive the prescription for the drug. As noted above, only limited amounts of the drug may be prescribed to the patient, with no refill prescriptions being permitted. The pharmacy may not receive more drug for distribution unless he can account for all drug previously dispensed. Also, the pharmacy may only continue to distribute the drug to registered patients who have prescriptions from registered pharmacies.

Various modifications of the invention, in addition to those described herein, will be apparent to those skilled in the art from the foregoing description. Such modifications are also intended to fall within the scope of the appended claims.

What is claimed:

1. A method for delivering a teratogenic drug to patients in need of the drug while avoiding the delivery of said drug to a foetus comprising:
   a. registering in a computer readable storage medium prescribers who are qualified to prescribe said drug;
   b. registering in said medium pharmacies to fill prescriptions for said drug;
   c. registering said patients in said medium, including information concerning the ability of female patients to become pregnant and the ability of male patients to impregnate females;
   d. retrieving from said medium information identifying a subpopulation of said female patients who are capable of becoming pregnant and male patients who are capable of impregnating females;
   e. providing to the subpopulation, counseling information concerning the risks attendant to fetal exposure to said drug;
   f. determining whether patients comprising said subpopulation are pregnant; and
   g. in response to a determination of non-pregnancy for said patients, authorizing said registered pharmacies to fill prescriptions from said registered prescribers for said non-pregnant registered patients.

2. The method of claim 1 wherein said drug is thalidomide.

3. The method of claim 1 further comprising including in said registering information concerning male patients who are capable of impregnating females and including said males within said subpopulation.

4. The method of claim 1 wherein said determination comprises pregnancy testing.

5. The method of claim 1 wherein the issuance and fulfillment of said prescriptions are recorded in said computer readable storage medium.

6. The method of claim 1 wherein refilling of said prescriptions is authorizable only in response to information contained on said computer readable storage medium.

7. The method of claim 1 wherein said prescriptions are filled for no more than about 28 days.

8. The method of claim 1 wherein said prescriptions are filled together with distribution of literature warning of the effects of said drug upon foetuses.

9. The method of claim 1 further comprising providing said patients with contraception counseling.

10. The method of claim 1 further comprising:

h. providing to said patients who are capable of becoming pregnant a contraceptive device or formulation.

* * * * *

(12) INTER PARTES REVIEW CERTIFICATE (1913th)
United States Patent (10) Number: US 6,045,501 K1
Elsayed et al. (45) Certificate Issued: Feb. 17, 2021

(54) METHOD FOR DELIVERING A DRUG TO A PATIENT WHILE PREVENTING THE EXPOSURE OF A FOETUS OR OTHER CONTRAINDICATED INDIVIDUAL TO THE DRUG

(75) Inventors: Marc Elsayed; Bruce Williams

(73) Assignee: CELGENE CORPORATION

Trial Number:

IPR2015-01092 filed Apr. 23, 2015

Inter Partes Review Certificate for:

Patent No.: 6,045,501
Issued: Apr. 4, 2000
Appl. No.: 09/143,569
Filed: Aug. 28, 1998

The results of IPR2015-01092 are reflected in this inter partes review certificate under 35 U.S.C. 318(b).

INTER PARTES REVIEW CERTIFICATE
U.S. Patent 6,045,501 K1
Trial No. IPR2015-01092
Certificate Issued Feb. 17, 2021

AS A RESULT OF THE INTER PARTES REVIEW PROCEEDING, IT HAS BEEN DETERMINED THAT:

Claims 1-10 are cancelled.

\* \* \* \* \*